US00PP13527P2

(12) United States Plant Patent
Zaiger et al.

(10) Patent No.: US PP13,527 P2
(45) Date of Patent: Jan. 28, 2003

(54) PEACH TREE NAMED 'SIERRA SNOW'

(76) Inventors: Gary Neil Zaiger, 1907 Elm Ave., Modesto, CA (US) 95358; Grant Gene Zaiger, 4005 California Ave., Modesto, CA (US) 93538; Leith Marie Gardner, 1207 Grimes Ave., Modesto, CA (US) 95358

( * ) Notice: Subject to any disclaimer, the term of this patent is extended or adjusted under 35 U.S.C. 154(b) by 0 days.

(21) Appl. No.: 10/055,696

(22) Filed: Jan. 25, 2002

(51) Int. Cl.[7] ..... A01H 5/00
(52) U.S. Cl. ..... Plt./195
(58) Field of Search ..... Plt./195

*Primary Examiner*—Bruce R. Campell
*Assistant Examiner*—Anne Marie Grünberg

(57) ABSTRACT

A new and distinct variety of peach tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consists of the following combination of desirable features:

1. Vigorous, upright growth habit.
2. Heavy and regular production of fruit.
3. Fruit with a high degree of attractive red skin color.
4. Fruit with mild, sweet, sub-acid, white flesh.
5. Firm fruit with good shipping and storage abilities.

1 Drawing Sheet

STATEMENT REGARDING FEDERALLY SPONSORED RESEARCH AND DEVELOPMENT

Not applicable.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of peach (*Prunus persica*) tree was originated and asexually reproduced by us in our experimental orchard loacted near Modesto, Stanislaus County, Calif.

Prior Varieties

Among the existing varieties of peach and nectarine trees, which are known to us, and mentioned herein, are 'May Grand' Nectarine (U.S. Plant Pat. No. 2,794) and 'Snowbrite' Peach (U.S. Plant Pat. No. 8,195).

ORIGIN OF THE VARIETY

The present new peach (*Prunus persica*) variety was developed by us in our experimental orchard, located near Modesto, Calif., as a first generation cross between a proprietary parent with the field number 36EB86 and 'Snowbrite' Peach (U.S. Plant Pat. No. 8,195). The maternal parent 36EB86 originated from a cross between a seedling selection from 'May Grand' Nectarine (U.S. Plant Pat. No. 2,794) crossed with a peach of unknown paentage. We planted and maintained a large group of these first generation seedlings on their own root system, under close and careful observation, during which time we recognized the desirable fruit characteristics of the present variety and selected it in 1994 for asexual propagation and commercialization.

ASEXUAL REPRODUCTION OF THE VARIETY

Asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of peach tree is of large size, vigorous, upright growth and is a regular and productive bearer of large size, white flesh, clingstone fruit with good storage and shipping qualities. The fruit is further characterized by its attractive red skin color, firm flesh, mild, sweet, sub-acid flavor with very good eating quality, and in comparison to 'Snowbrite' Peach (U.S. Plant Pat. No. 8,195), the fruit of the new variety is larger in size and is approximately 7 days later in maturity.

PHOTOGRAPH OF THE VARIETY

The accompanying color photographic illustration shows typical specimens of the foliage and fruit of the present new peach variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in color representation of this type.

DESCRIPTION OF THE VARIETY

The following is a detailed botanical description of the new variety of peach tree, its flowers, foliage and fruit as based on observations of 5 year old specimens grown on 'Nemaguard' Rootstock (non-patented), near Modesto, Calif., with color in accordance with Munsell Book of Color.

Tree:

*Size.*—Large. Normal for peach trees.

*Vigor.*—Vigorous. Growth of 1.5 to 2 meters in height the first growing season. Varies with fertility of soil and cultural practices.

*Form.*—Upright. Usually pruned to vase shape for increased sunlight penetration.

*Branching habit.*—Upright. Width of tree increases with heavy production of fruit. Crotch angle approximately 30°.

*Productivity.*—Productive. Fruit thinning and spacing necessary for marketable size fruit.

*Bearer.*—Regular. Has produced adequate fruit set for 4 consecutive years. No alternate bearing observed.

*Fertility.*—Self-fertile.

*Density.*—Medium dense. Pruning to open center of tree is desirable for healthy fruit wood and to provide fruit with sunlight and heat units for higher soluble solids (Brix).

*Hardiness.*—Tree grown in USDA Hardiness Zone 9. Winter chilling requirement approximately 800 hours at or below 45° F. Hardy in all stone fruit growing areas of California.

Trunk:

*Size.*—Large, stocky. Average circumference of 59.7 cm at 30.5 cm above the ground.

*Texture.*—Medium shaggy, becoming rougher with age.

*Color.*—10YR 3/2 to 10YR 5/2.

Branches:

*Size.*—Medium stocky. Average circumference of 16.51 cm at 121.9 cm above ground.

*Surface texture.*—New growth smooth, varies to medium rough with age.

*Lenticels.*—Average number of 34 in a 25.8 square cm area. Average length 4.3 mm. Average width 2.1 mm. Color 5YR 5/10 .

*Color.*—New growth 2.5GY 5/6 to 2.5GY 6/6. Old growth 2.5Y 3/4 to 2.5Y 4/4, becoming darker with age.

Leaves:

*Size.*—Large. Average length 169.5 mm. Average width 42.8 mm.

*Form.*—Lanceolate.

*Apex.*—Acuminate.

*Base.*—Cuneate.

*Margin.*—Serrate.

*Thickness.*—Medium.

*Surface texture.*—Upper surface relatively smooth, slightly indented over midrib and leaf veins, glabrous. Lower surface relatively smooth, small ridges created by mid rib and pinnate venation, glabrous.

*Petiole.*—Average length 10.7 mm. Average width 1.9 mm. Color 5GY 6/8. Grooved longitudinally.

*Glands.*—Reniform. Number varies from 4 to 9, average number 6. Medium to large size. Average length 1.5 mm. Average width 0.8 mm. Located on the base of the leaf blade and on the upper portion of the petiole. Color 10Y 8.5/6.

*Color.*—Upper surface 7.5GY 3/4. Lower surface 7.5GY 5/4. Midvein color 5GY 7/8.

Flower buds:

*Size.*—Large. Average length 16.9 mm. Average width 9.2 mm.

*Hardiness.*—Hardy in all stone fruit growing areas of California.

*Form.*—Plump, conical, becomes elongated before opening.

*Pedicel.*—Medium. Average length 3.2 mm. Average width 2.3 mm. Color 5GY 7/6 .

*Color.*—10RP 6/12.

Flowers:

*Size.*—Large, showy. Average height 21.2 mm. Average diameter 43.3 mm.

*Petals.*—Number 5, alternately arranged to sepals. Orbicular shape. Average length 17.2 mm. Average width 16.2 mm. Color 5RP 7/10. Margin — Sinuate, slightly cupped.

*Sepals.*—Number 5, alternately arranged to the petals. Ovate, apex rounded. Inner surface glabrous, outer surface pubescent. Average length 4.4 mm. Average width 4.0 mm. Color — upper surface 5GY 5/6, lower surface 5RP 2/8.

*Stamens.*—Average number per flower 41. Average length 13.2 mm. Filament color N9/0.5. Anther color 6.25R 4/12.

*Pollen.*—Self fertile.

*Pistil.*—Pubescent. Average length 17.4 mm. Average height 3.3 mm lower than stamens. Color 10 Y 8.5/6.

*Fragrance.*—Slight.

*Blooming period.*—Date of First Bloom Mar. 5, 2001. Date of Petal Fall Mar. 15, 2001. Varies slightly with climatic conditions.

*Color.*—5RP 7/8. Varies with age of bloom.

*Number of flowers per flower bud.*—One.

*Pedicel.*—Short in length. Average length 3.7 mm. Average width 2.3 mm. Color 5GY 6/6.

Fruit:

*Maturity when described.*—Firm, ripe.

*Date of first picking.*—Jun. 17, 2001.

*Date of last picking.*—Jun. 24, 2001. Varies slightly with climatic conditions.

*Size.*—Large. Average diameter axially 69.8 mm. Average transversely in suture plant 73.2 mm. Average weight 232.8 grams. Average weight varies slightly with fertility of the soil, amount of thinning and climatic conditions.

*Form.*—Globose, nearly rounded.

*Suture.*—Shallow, extends from base to apex.

*Ventral surface.*—Rounded, nearly smooth.

*Apex.*—Usually rounded, some fruit with very slight pistil point.

*Base.*—Slightly retuse.

*Cavity.*—Rounded to slightly elongated in suture plane. Average depth 6.3 mm. Average diameter 9.4 mm.

Stem:

*Size.*—Small. Average length 7.9 mm. Average diameter 3.1 mm.

*Color.*—2.5GY 5/4 .

Flesh:

*Ripens.*—Evenly, only slightly earlier at the apex.

*Texture.*—Firm, meaty.

*Fibers.*—Few, small and tender.

*Aroma.*—Slight.

*Amydgalin.*—Undetected.

*Eating quality.*—Very good.

*Flavor.*—Very good, mild, sweet, sub-acid.

*Juice.*—Moderate amount, sweet, sub-acid, enhances flavor.

*Brix.*—10.3°, varies slightly with amount of fruit per tree and climatic conditions.

*Color.*—2.5Y 9/2. Pit cavity color varies from 5Y 8/4 to 5Y 8/6.

Skin:

*Thickness.*—Medium.

*Surface.*—Smooth, without roughness or reticulation.

*Down.*—Pubescent, relatively short.

*Tendency to crack.*—None.

*Color.*—Ground color 5Y 9/2, overspread with 5R 4/8 to 5R 5/12.

*Tenacity.*—Tenacious to flesh.

*Astringency.*—None.

Stone:

*Type.*—Clingstone.

*Size.*—Large. Average length 32.1 mm. Average width 23.9 mm. Average thickness 18.9 mm.

*Form.*—Obovate.

*Base.*—Rounded.

*Apex.*—Acuminate, short in length. Average length 3.45 mm.

*Surface.*—Irregularly furrowed toward the apex, pitted toward the base. Pit cavities vary from round to elongated. One long groove on each side of suture.

*Sides.*—Equal to unequal. Some stones have one side slightly larger, extending further from the suture plane.

*Tendency to split.*—None.

*Color.*—Varies from 7.5YR 6/4 to 7.5YR 6/8 when dry.

Kernal:

*Form.*—Ovate.

*Taste.*—Bitter.

*Viability.*—Viable, embryo developed.

*Size.*—Average length 15.9 mm. Average width 9.8 mm. Average thickness 4.4 mm.

*Skin.*—Color varies from 7.5YR 7/4 to 7.5YR 7/6.

Use: Dessert. Market — local and long distance.

Keeping quality: Good, held firm in cold storage at 38° to 42° F. for 21 days without internal flesh breakdown or loss of flavor.

Shipping quality: Minimal skin scarring or bruising of flesh during picking and packing trials.

Plant disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A substantially new and distinct variety of peach tree, substantially as illustrated and described, characterized by its large size, vigorous upright growth and is a regular and productive bearer of large size, white flesh, clingstone fruit that has a mild, sweet, sub-acidic flavor; the fruit is further characterized by its attractive red skin color, very good eating quality and, in comparison to 'Snowbrite' Peach (U.S. Plant Pat. No. 8,195), the fruit of the new variety is larger in size and is approximately 7 days later in maturity.

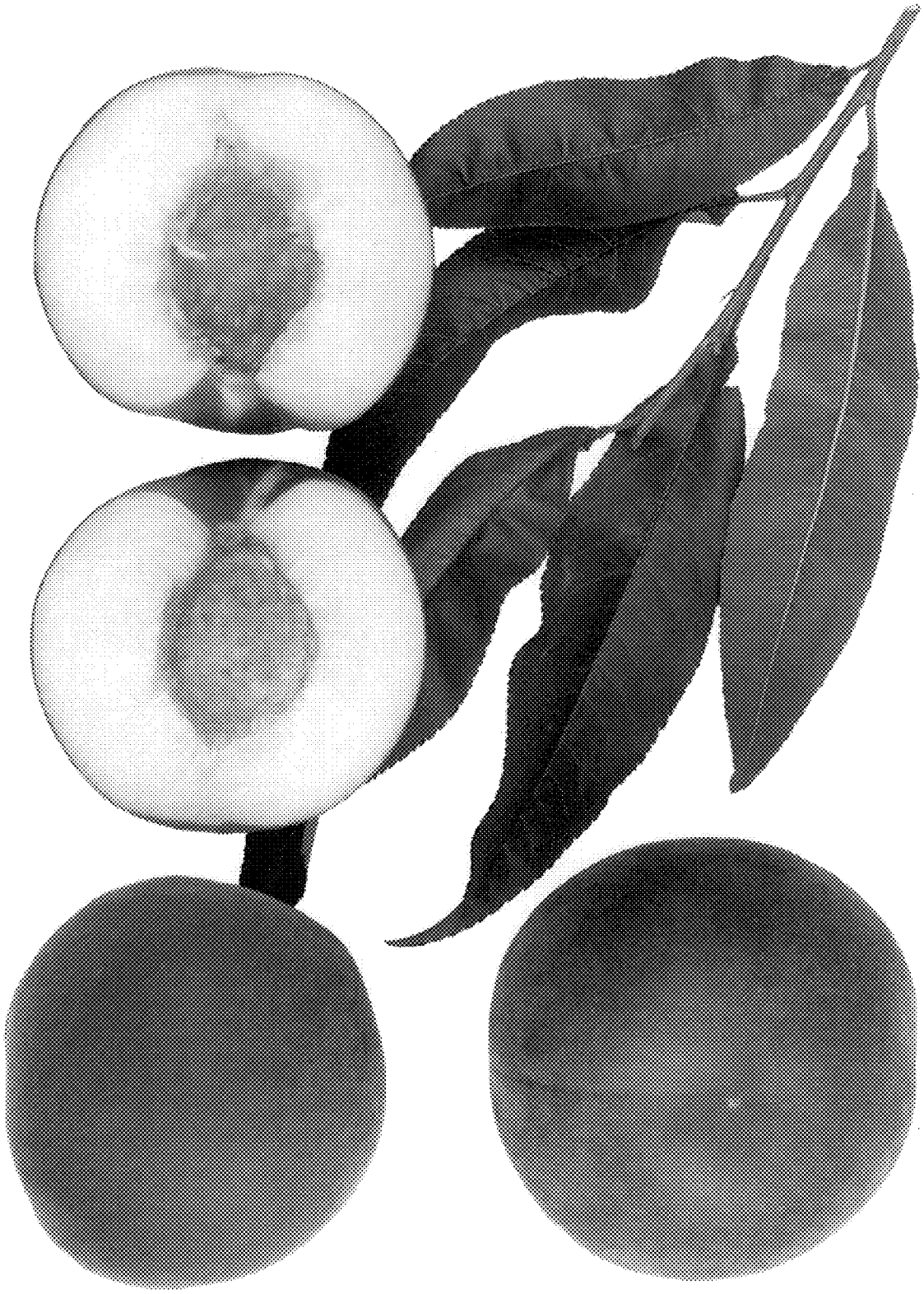

* * * * *